United States Patent [19]

Betts

[11] Patent Number: 4,991,439

[45] Date of Patent: * Feb. 12, 1991

[54] APPARATUS FOR DETECTING INSECT-INDUCED VIBRATIONS IN PARTICULATE MATTER

[75] Inventor: William B. Betts, Alva, Okla.

[73] Assignee: B & B Industries, Alva, Okla.

[*] Notice: The portion of the term of this patent subsequent to Jan. 23, 2007 has been disclaimed.

[21] Appl. No.: 272,857

[22] Filed: Nov. 18, 1988

[51] Int. Cl.⁵ ............................................. G01N 29/00
[52] U.S. Cl. .......................................... 73/587; 73/661
[58] Field of Search .................. 73/584, 587, 591, 632, 73/659, 661; 310/327, 334, 336

[56] References Cited

U.S. PATENT DOCUMENTS

| | | | |
|---|---|---|---|
| 2,875,354 | 2/1959 | Harris | 310/8.2 |
| 3,166,730 | 1/1965 | Brown, Jr. et al. | 340/10 |
| 4,008,711 | 2/1977 | Olinger et al. | 128/2 K |
| 4,629,834 | 12/1986 | Waggoner et al. | 381/68.2 |
| 4,671,114 | 6/1987 | Litzkow et al. | 73/587 |
| 4,701,658 | 10/1987 | Ringermacher et al. | 310/334 |

OTHER PUBLICATIONS

R. C. Barton, "An Audio-Amplifying System for Termite Detection", *Termite and Termite Control*, 1934, pp. 711-714.

Roy J. Pence, "Electronic Detective Developed by UCLA Uncovers Termites", *Pest Control*, Nov. 1954, p. 27.

"Electronic Termite Detection", *Physionics Corporation*, (publication date unknown).

Primary Examiner—John Chapman
Attorney, Agent, or Firm—Jerry M. Keys

[57] ABSTRACT

Grain-destroying insects, and those which may infect other types of particulate matter, when feeding and moving about, induce vibrations in the grain or particulate material affected which is modified and amplified to an audible level. The detection is performed using a crystal with piezoelectric properties directly and physically connected to a vibratory receiving structure such as an elongated probe, a thin, flat diaphragm or the like which mechanically amplifies the vibrations to the crystal. The vibratory sounds are then analyzed, such as by comparison with other records of known destructive insects to determine the probable species of insect and its location.

21 Claims, 4 Drawing Sheets

U.S. Patent  Feb. 12, 1991  Sheet 1 of 4  4,991,439
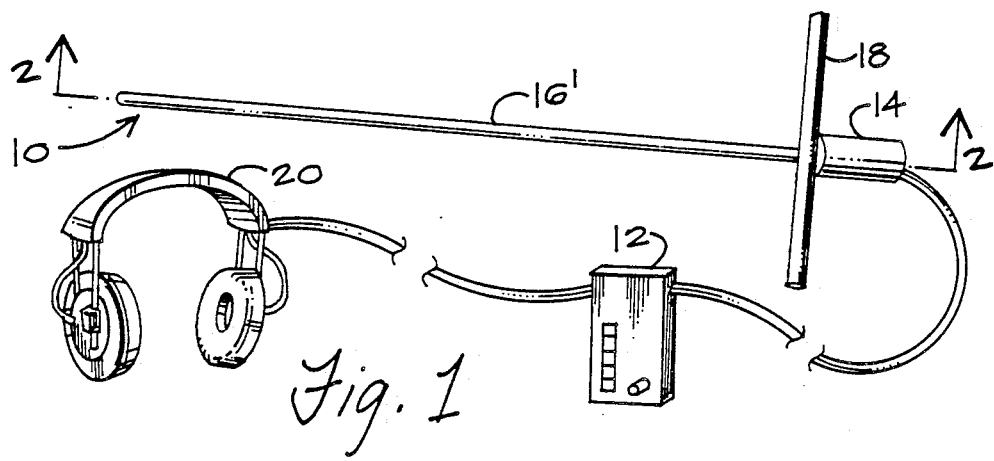
Fig. 1
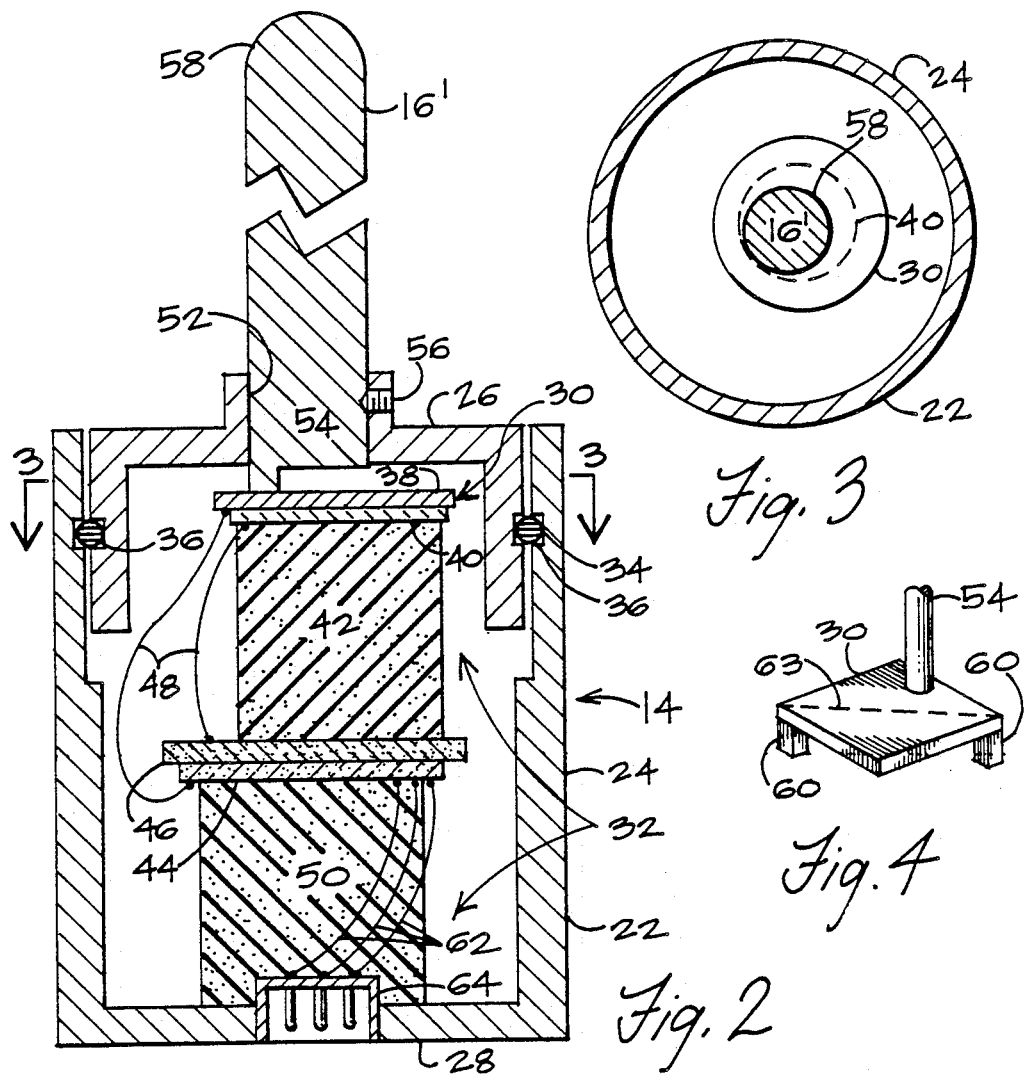
Fig. 3
Fig. 2
Fig. 4

APPARATUS FOR DETECTING INSECT-INDUCED VIBRATIONS IN PARTICULATE MATTER

CROSS-REFERENCE TO RELATED APPLICATION

This application is related to my co-pending patent application Ser. No. 07/136,843 filed Dec. 22, 1987, now U.S. Pat. No. 4,895,025, which is a continuation-in-part of my application Ser. No. 06/906,880 filed Sept. 15, 1986, now abandoned.

FIELD OF THE INVENTION

The present invention relates to apparatus and methods for detecting and locating insects, and more particularly relates to apparatus and methods for detecting and locating destructive insects in particulate matter, such as grain, where the apparatus and methods employ an electric circuit for amplifying insect generated vibrations in the objects or matter being affected or destroyed.

As is well known, insect pests have been damaging or destroying food and other articles, such as grain and other particulate products, particularly foodstuffs, for centuries. Such insects are usually invisible, being contained by the articles being destroyed, and must be located and identified in order to provide some means of control and/or elimination. It frequently happens, as in the case of grain-destroying insects and termites, that extensive damage has been done before insect presence or the damage is detected.

This invention provides a portable electrical apparatus which includes a piezoelectric transducer for detecting and amplifying insect-or larva-produced vibrations and a method for identifying the kinds of insects and locating the position or proximity of insects destroying the product under test.

BACKGROUND OF THE INVENTION

Prior patents featuring vibratory sound amplification have generall related to stethoscopes in which a transducer is utilized for monitoring heart beats or the sound of blood produced in passing through heart valves, even detecting of fetal heart beats.

Although electronic devices for sensing insect-induced vibrations have been constructed in the past, such devices had only limited practicability due to the need for conflicting design parameters. Such devices need to be extremely sensitive to pick up the subtle vibrations in a structure or other article caused by insects. Yet if such sensitivity was achieved, the device also picked up a large variety of vibrations caused by other phenomena, as well as human activity. This has typically limited the usefulness of such prior art devices to laboratory-type environments.

R. C. Barton in "An Audio-Amplifying System for Termite Detection," *Termites and Termite Control*, 1934, pp. 711–714, discloses an early attempt to develop an audio-amplifying system for termite detection. The system used a phonograph-type needle as a probe which was actually inserted into the article under inspection, such as a wall, for detecting the mechanical vibrations in the object being inspected. The author apparently tried other transducers, such as an electrical stethoscope, but without the level of success that he had with the phonograph needle. The electrical signals from the needle transducer were then amplified and filtered prior to being transmitted to earphones. The article clearly indicates at p. 714, however, that the system was not successful out of a laboratory environment and, in addition, was too costly to be practical.

Another article also discloses a device for invasively detecting termites in a laboratory environment, Roy J. Pence, "Electronic Detective Developed by UCLA Uncovers Termites," *Pest Control*, Nov., 1954, p. 27. The device described in this article comprises a transducer having a needle probe which is actually inserted in the material to be inspected, and an amplifier which amplifies the portion of the electrical signals generated by the needle-type transducer which falls within a preselected frequency range. The article expressly indicates that its value is as a laboratory tool.

There is additionally a marketing brochure "Electronic Termite Detection", Physionics Corprtion, (publication date unknown), that discloses an electronic termite detector which comprises a hand-held probe-type transducer, an amplifier for amplifying electrical signals generated by the probe which are within a specified frequency range, and earphones. Although the initial Instructions in the brochure indicate that it is only necessary to hold the probe firmly against the surface being inspected, a subsequent supplement to the instructions states that the operator should use a Safety Needle which was included with the device, both to protect the probe and crystal element and to allow greater clarity in listening to termites, by eliminating any noise generated by operator contact with the probe. None of the devices described in the publications are suitable for detecting insects in particulate matter, such as wheat, rice, or the like.

The invention is distinctive over the prior art by providing a piezoelectric transducer mechanically and directly connected to a probe or noise detection structure capable of detecting vibrations or noise in particulate matter infested with insects or larvae. The inventive device minimizes the conversions of energy because of the direct physical contact between the vibration receiving structure and the piezoelectric crystal. The apparatus will detect sounds generated by the movement, eating or other destruction of flour beetles, rice weevils, Indian grain moths, and other grain destroying insects in grain bins, trucks or other storage areas, and amplify those sounds sufficiently to permit an operator to hear such vibrations through a headset. The frequency ranges of those movements vary from 350 to 3,500 Hertz, and in a narrower range from 750 Hertz to 1500 Hertz depending upon the grain (milo, corn, wheat, rice, flax, etc.) and the insect making the noise. The movement pattern made by different insects due to varying sizes and speed of movement makes it possible to analyze the patterns and identify which insect is making the noises picked up through the transducer.

SUMMARY OF THE INVENTION

Accordingly, it is an object of the present invention to provide an apparatus and method for detecting the presence of insects in particulate matter, such as grain.

It is another object of the present invention to provide an apparatus for detecting the presence of insects in particulate matter, where the apparatus has mechanical design features to increase its sensitivity.

It is yet another object of the invention to provide a method for detecting the presence of insects in particulate matter that is portable, and quick and convenient to employ in operation.

In carrying out these and other objects of the invention, there is provided, in one form, an apparatus for detecting the presence of insects in particulate matter having a vibration receiving structure physically contacting in an off-center location a piezoelectric transducer structure, such as a crystal, for directly detecting the vibrations in the particulate matter via the vibration receiving structure and generating electrical signals in response to the detected vibrations. The portions of the electrical signals representative of the frequency range of vibrations generated by insects which may be present in the particulate matter are then selectively amplified by an electronic amplifier or the like. Finally, the signals representative of the vibrations to identify the species within the particulate matter are analyzed.

BRIEF DESCRIPTION OF THE DRAWINGS

FIG. 1 is a perspective view of one aspect of the apparatus bearing an elongated probe;

FIG. 2 is a vertical cross sectional view of the transducer portion of the apparatus, at an enlarged scale, taken along the line 2—2 of FIG. 1;

FIG. 3 is a horizontal cross sectional view of the transducer portion of the apparatus, at an enlarged scale, taken along the line 3—3 of FIG. 2;

FIG. 4 is a perspective view of a square piezoelectric crystal and a configuration for mounting it;

It will be appreciated that some of the elements of the Figures, particularly FIGS. 1–6, are not to scale for clarity.

DETAILED DESCRIPTION OF THE INVENTION

Figure 5:
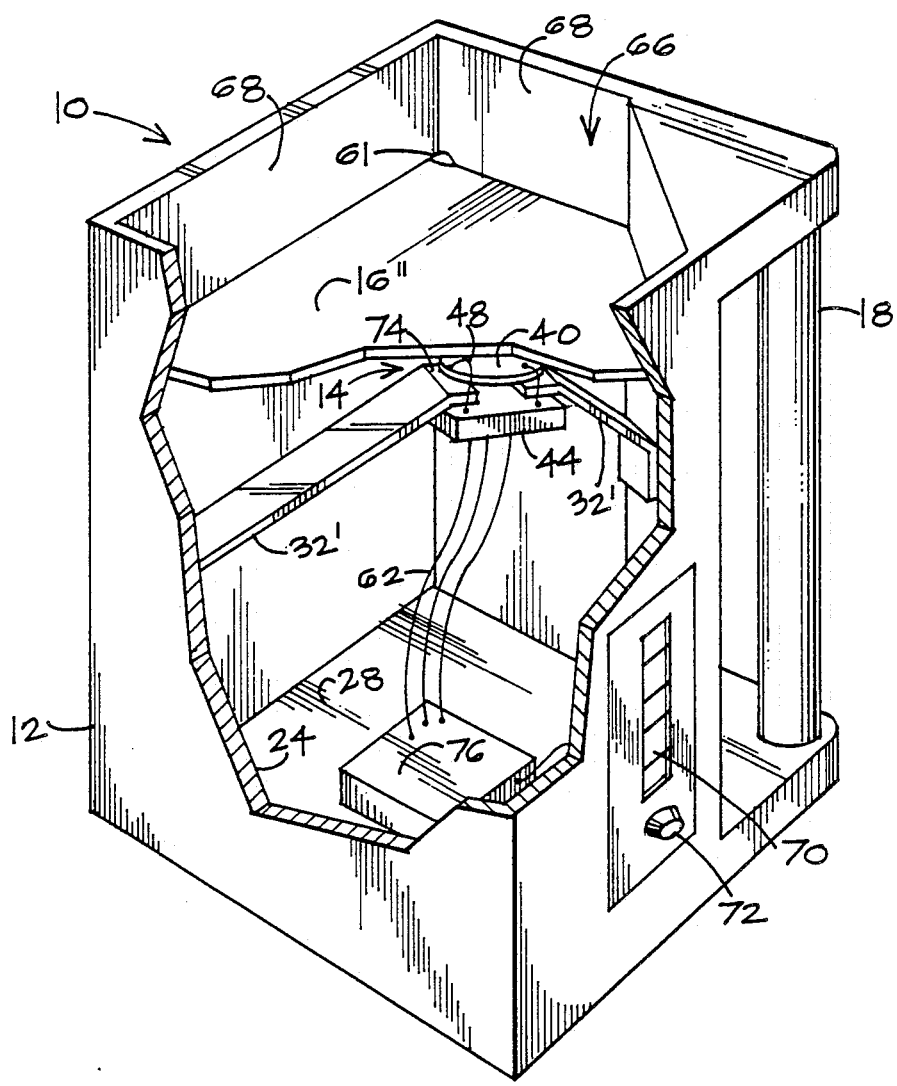
FIG. 5 is a perspective view of another aspect of the invention having a bin for containing the particulate matter to be tested.

The invention will now be described in more detail with reference to the various Figures. Like characters of reference designate like parts in those Figures of the drawings in which they occur.

In the drawings:

The reference numeral 10 indicates generally the apparatus for detecting insect-induced vibrations in particulate matter, which includes a circuit-containing housing 12, a transducer 14 having a vibration receiving structure 16 in the form of an elongated probe and a handle 18, and earphones or headset 20 connected with the circuit contained by housing 12.

Referring more particularly to FIG. 2, the transducer 14 has a cylindrical dielectric case or housing 22 having an annular wall 24 and closed ends 26 and 28 which loosely surround a piezoelectric transducer assembly 30 and its mounting means 32. Closed end 26 may be resiliently mounted within annular wall 24 by means of O-ring 34 which provides a sealing but flexible connection between corresponding grooves 36 in end 25 and wall 24.

The piezoelectric transducer assembly 30 is, in one aspect, generally circular of a smaller diameter than the inside diameter of case 22, and comprises a plurality, preferably at least two, layers in superposition. The top layer 38, as viewed in FIG. 2, is a conductive metal, such as silver, copper, brass or the like and the next or bottom layer 40 is a piezoelectric material, which may be formed from either natural or man-made crystals or ceramic materials or a combination thereof. It will be appreciated that piezoelectric assembly 30 may be composed of many layers, including a plurality of same or different metals and/or a plurality of the same or different piezoelectric materials. It is well known in the art of piezoelectric crystals that various layer combinations or sandwiches may be utilized to advantage, and the invention herein is not limited to a particular one.

The crystal assembly 30 also may be a rectangular bar or a square, as well as a circular device so long as the stress placed on the piezoelectric material causes the strain on the piezoelectric material to operated in the direction needed to cause piezoelectric activity. A round or square shape is preferred because it has been found that such shapes will not break as easily under stress as a bar-shaped piezoelectric assembly.

The piezoelectric assembly 30 is axially supported, as a unit, in the transducer case 22 by mounting assembly 32, which, in one aspect, comprises a nonconductive mounting platform 42. Mounting platform 42 may be a hard rubber or a foam rubber so that piezoelectric assembly 30 may be allowed to move relatively freely within case 22. If a pre-amp 44 to eliminate 60-cycle hum is included within transducer housing 22, it may take the form of discrete component or integrated circuit chip 46 placed as close as possible to piezoelectric assembly 30 and connected thereto by wires 48, as shown in FIG. 2. Thus, secondary mounting platform 50, also made from foam rubber, may be used to mount chip 46 within the case 22 to impart more resiliency to piezoelectric assembly 30.

The case end 26 is centrally apertured at 52 for surrounding the vibration receiving structure 16, which, in this aspect, is a long, solid probe 16'. The proximal end 54 of vibration receiving probe 16 directly and physically contacts piezoelectric assembly 30 and may be secured with respect to case end 26 by a fastening device 56, such as a set screw. An important feature of the invention is that proximal end 54 of vibration receiving structure 16 is not connected to the center of piezoelectric crystal assembly 30, but is mounted off-center thereto. Indeed, the proximal end 54 may be milled or undercut to the shape seen in FIG. 2 which helps accentuate the amplifications and increase the shear force on crystal 40. Alternatively, proximal end 54 may retain a uniform cross section with the rest of probe 16' and simply contact assembly 30 off-center, with an optional mounting point provided. This off-center mounting by any means helps to mechanically amplify the received vibrations. The free or distal end 58 of the vibration receiving probe 16' projects beyond the plane of case end 26.

There may also be provided one or more mounting points providing flexible connection between piezoelectric assembly 30 and end 26 attached to probe 16'. Mounting point may be made of hard or foam rubber or the like. The number of these mounting points should be minimized to prevent damping of the vibrations that are detected. In a preferred aspect, no more than two such mounting points are present to permit the crystal assembly 30 to move more freely with any received motion. Three or more mounting points may undesirably stabilize the piezoelectric assembly 30.

Distal end 58 of probe 16' is to be inserted into a quantity of particulate material that may be contained in a bin or truck or the like. The length of probe 16' is considerably greater than its width, and it will be appreciated that probe 16' is designed to act as a moment arm with respect to piezoelectric crystal assembly 30. The invention is not limited to a particular length to width ratio of probe 16' although a length/width ratio range of from approximately 30/1 to 130/1 or more may be used to advantage.

The vibration receiving structure 16 in the form of the elongated probe may be of any lightweight metal that may transmit very small vibrations of grain destroying insects or the like. In one embodiment, probe 16 may be a solid piece of ⅜" aluminum about three feet long. Other metals may be used if they are light enough and could transduce sounds in the frequency ranges of 350 to 3,500 Hertz, preferably 750 to 1,500 Hz. Aluminum does the job well and is inexpensive, easy to machine, but the invention is not limited to aluminum. It is important for the probe 16' to be continuous and not welded or threaded together at any point as this will reduce the probe 16"s ability to pass along vibrations by the movement of insects to the piezoelectric crystal assembly 30.

A handle 18 may be provided to probe 16' by which transducer 14 also may be carried to reduce stress on the piezoelectric assembly 30, as shown in FIG. 1. This handle 18 will also assist in inserting the probe 16' into a mass of particulates to further minimize stress to the piezoelectric assembly 30.

Since stress will be applied through the probe 16' to the piezoelectric crystal assembly 30 when the probe 16' is placed in a quantity of particulates, such as grain, the foam rubber mounting platforms 42 and/or 50 cushions the impact of any stress transmitted through the probe 16' to the piezoelectric assembly 30, thereby essentially allowing the piezoelectric assembly 30 and probe 16' to "float" within the case 22. It should be noted, however, that other resilient materials or structures that allow the piezoelectric assembly 30 to essentially float within the case 22 may also be substituted for the foam rubber 42 and 50.

Two wires 48 are connected to either side of the piezoelectric assembly 30. The wires 48 are kept short in accordance with conventional practice to minimize unwanted currents from being induced into the circuit, and the other ends of the wires are connected to a pre-amp 44. Pre-amp 44 may be any conventional preamplifier that is made up of discrete components or fabricated on an integrated circuit chip 46. In one aspect, a gain of approximately 1000 times input is provided by pre-amp 44. The signal from pre-amp 44 is sent to the pre-amps and audio amps located in circuit housing 12 via wires 62 and connector 64 in end 28 of case 22.

Shown in FIG. 3 is a cross section of transducer 14 taken along line 3—3 of FIG. 2. This FIG. 3 illustrates the off-center connection of the distal end 58 of vibration receiving probe 16 with piezoelectric assembly 30 bearing crystal 40. This off-center orientation aids in the mechanical amplification of any vibration detected. A possible position for a single mounting point is also illustrated, although another position may be utilized, of course. FIG. 4 shows an off-center mounting position for a square piezoelectric assembly 30. Note distal end 54 of probe 16 is also not on a line 63 connecting the two mounting points 60.

Illustrated in FIG. 5 is another aspect of the invention in the form of a particulate or grain bin apparatus 10, having a housing 12, which also serves as transducer case, a transducer 14 within housing 12, a vibration receiving structure 16" which forms at least one interior surface (illustrated as the bottom) of container or bin 66 within grain bin apparatus 10. Bin 66 also has a plurality of other walls 68, which may be annular or rectilinear, for example. In this version, handle 18 is not directly connected to vibration receiving structure 16", but is an integral part of housing 12. Headphones are not shown herein, but an equivalent mechanism is light-emitting diode (LED) display 70 which provides operator-interpretable information. Alternatively, or in addition to LED display 70, a conventional external speaker or headphone phono jack (not shown) may be provided connected with a volume control 72.

Walls 24 of case 12 are rectilinear in this embodiment, and they meet with closed end 28. Piezoelectric crystal 40 is in intimate, direct and mechanical connection with the undersurface of vibration receiving structure 16", which in this case is a flat diaphragm with its edges and/or corners connected to walls 24 of case 12. Diaphragm 16" may be slightly flexed or stressed by mounting piezoelectric crystal 40 slightly below the plane of the diaphragm 16". This causes tension on the diaphragm 16" and aids in the mechanical amplification of any sounds made thereon. This diaphragm 16" has been fabricated out of brass stock with success to serve as a physical filter, mechanical amplifier and damping device since it is somewhat selectively sensitive to vibrations in the desired frequency range. Brass is also cheap, long lasting and easy to work with. The diaphragm 16" of brass shim stock 0.003" thick and 6" long by 4" was found to help limit frequencies below the VHF range, which property helps the electronic filtration in the pre-amps.

Piezoelectric crystal 40 is shown mounted off-center of the diaphragm 16", for reasons discussed above. The more mounting points 61 used in securing the diaphragm 16", the more stable and less sensitive to vibration it will be. If corners of the diaphragm 16" are attached, it is recommended that two non-adjacent corners be used. If points along the side of the diaphragm 16" are to be secured, it is suggested that non-symmetrical positions be employed.

A resilient mounting means 32 may also be incorporated in the version of the invention shown in FIG. 5. Illustrated are mounting means 32 in the form of struts or braces that are preferably made of a hard plastic or metal that would mechanically amplify any vibrations received by diaphragm 16", rather than damp or suppress such vibrations. A secondary mounting point 74 may connect crystal 40 with the mounting means, though again it is recommended that the number of mounting points 74 be minimized and their relative positions be non-symmetrical, as discussed above.

As in the embodiment shown in FIG. 2, crystal 40 is connected to a nearby pre-amp 44 via connecting wires 48. Pre-amp 44 is in turn connected to electronic circuitry 76 containing an additional pre-amp and/or audio amps by connecting wires 62, as will be discussed in more detail below. In this fashion, the bin apparatus 10 of FIG. 5 is similar to the embodiment in FIG. 1 in equivalent structures.

Figure 6:
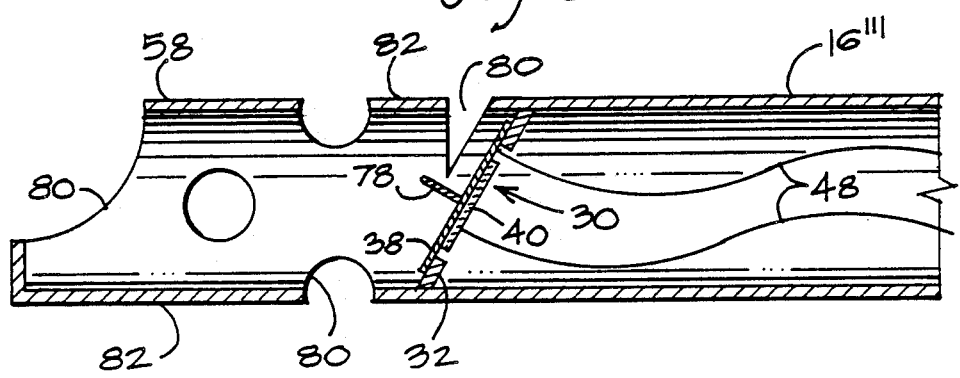
FIG. 6 is a cross sectional view of another aspect of the invention illustrating a probe end.

Shown in FIG. 6 is another embodiment of an apparatus for detecting insect-induced vibrations in detail. This embodiment is similar to that illustrated in FIG. 1, except that in this embodiment, the structure 16 is a long, hollow tube whose distal end 58 is depicted in cross section in FIG. 6. Another difference is that piezoelectric assembly 30 is moved up structure 16 toward the distal end 58, rather than remaining in casing 22. While structure 16 is shown as hollow in FIG. 6, it is preferred that the probe be solid. No embodiment of the invention should rely upon using an air cavity to transmit the vibration in the manner of a wave guide. Conversion of mechanical vibration to acoustic vibration and then to electrical signals is not desired as some energy is lost in each conversion.

Piezoelectric assembly 30 is again comprised of at least a top layer 38, possibly metal, and a bottom layer 40 of piezoelectric crystal, shown in FIG. 6. Piezoelectric assembly 30 is again supported by mounting means 32, which may be of similar flexible material to that used in the FIG. 5 embodiment. Crystal 40 is again connected to optional pre-amp 44 (not shown) via connecting wires 48. Piezoelectric assembly 30 may also be provided with a small probe 78 or moment arm to increase the sensitivity of the apparatus 10. Additionally, distal end 58 of the structure 16 may also be provided with a plurality of holes 80 to permit entry of the particulates into the probe 16 for more intimate contact with piezoelectric assembly 30. However, it is suggested that the holes 80 not be so large as to eliminate some shielding or protection of assembly 30 and probe 78 by the probe wall 82 so that the assembly 30 or probe 78 are not damaged upon insertion into the mass of particulate matter. Angling assembly 30 with respect to the long dimension of structure 16, at 45°, for example, may also increase the sensitivity of the apparatus 10 to vibration. It will be appreciated that the exact configuration of the structure 16 and the placement of piezoelectric assembly 30 may vary with the application and may be left to the designer, now that the basic elements of the invention are known.

Diaphragms 16" similar to that of diaphragm 74 of copending application Ser. No. 07/136,843, incorporated by reference herein, may be used in the FIG. 5 version of the invention. The piezoelectric assembly 30 of the embodiments shown in FIGS. 5 and 6 are again preferably of circular or square shape for reasons discussed previously.

Due to the subtle nature of the insect vibrations sought to be detected, the piezoelectric assembly 30 should be mounted and positioned to generate significant strain in the piezoelectric materials for only very small variations in the stress applied through the vibration receiving structure 16. It has been discovered that sensitivity to such minor stress forces may be enhanced by mounting the piezoelectric assembly 30 to the mounting means 32 so that the piezoelectric assembly becomes unbalanced when stress is applied through the probe 78 to an off center point on the assembly 30 and the proximal end 54 in the FIG. 1 version or the diaphragm 16" contact in the FIG. 5 version, is attached to the top layer 38 of the piezoelectric assembly 30 at a point which creates shear, as well as compressive forces on the piezoelectric material 40.

With respect to a circular-shaped piezoelectric assembly 30, the circular assembly 30 may be mounted to the respective mounting means 32 or other structure at one or more points, such as mounting points 60, and the proximal end 54 of the probe 16 or a point of the diaphragm 16" of FIG. 5 is attached to the piezoelectric assembly 30 by suitable means to a point off center of the mounting point 60, if one, or off center from any line segment between any plurality of mounting points 60. The stress forces applied through a probe 16' or diaphragm 16" to the off center point of the assembly 30 will generate more strain in the piezoelectric crystal 40 due to the unbalanced application of the stress forces through the vibration receiving structure 16. See, for example, FIG. 3.

With respect to a square piezoelectric assembly 30, the square is mounted to the mounting assembly 32 at only two non-adjacent corners and the vibration receiving structure 16 is attached to the square piezoelectric assembly 30 at a point off the diagonal line between the two points at which the square piezoelectric assembly is attached to the mounting assembly. See, for example, FIG. 4.

The pre-amp 44 is available to eliminate 60 cycle hum that may be induced into the circuit. As noted, this pre-amp 44 should be physically located as close as possible to the piezoelectric crystal 40, as illustrated in FIGS. 2 and 5 also to minimize this induction. In one aspect pre-amp 44 is formed by an IC chip No. 741 op-amp, and the resistors and capacitors are sized appropriately to produce a gain of approximately 1,000 times the input. This pre-amp is conventional, and may be similar to the first and second stage pre-amps described below.

The amplification circuit 84 of the invention may be provided in three stages, in one aspect. The signal from the pre-amp 44 is sent to the first stage and second stage pre-amps 86 and 88, respectively, and audio amplifiers 90, which may be located in another container, such as housing 12 of FIG. 1. First stage pre-amp 86 may be a conventional IC chip No. LM 1458, which amplifies the signal approximately 21 times with the aid of appropriate resistors and capacitors according to standard practice, in one aspect of the invention. A possible circuit for the first stage pre-amp 86 is schematically illustrated on the left side of FIG. 7, although other circuits may be employed within the scope of this invention.

Employing the second stage 88, schematically illustrated in one embodiment in FIG. 7, the signal is then filtered with a standard butterworth configuration as a bandpass filter to exclude signals below 500 Hertz and signals above 1,500 Hertz, in one version. Then the signal is put through the next part of the pre-amp and amplified approximately 10 more times with the appropriate resistors and capacitors. The circuit 88 is operated with an open feedback for peak amplification. The signal is then sent to the third stage, in one aspect illustrated in FIG. 8, which may encompass a standard audio-amp, such as an IC chip No. LM 386 with the resistors and capacitors specified to amplify approximately another 20 times, for example only. This signal is then great enough to be listened to through headphones 20, to be recorded using tape recorders, or analyzed by computers to identify the insects.

Figure 7:
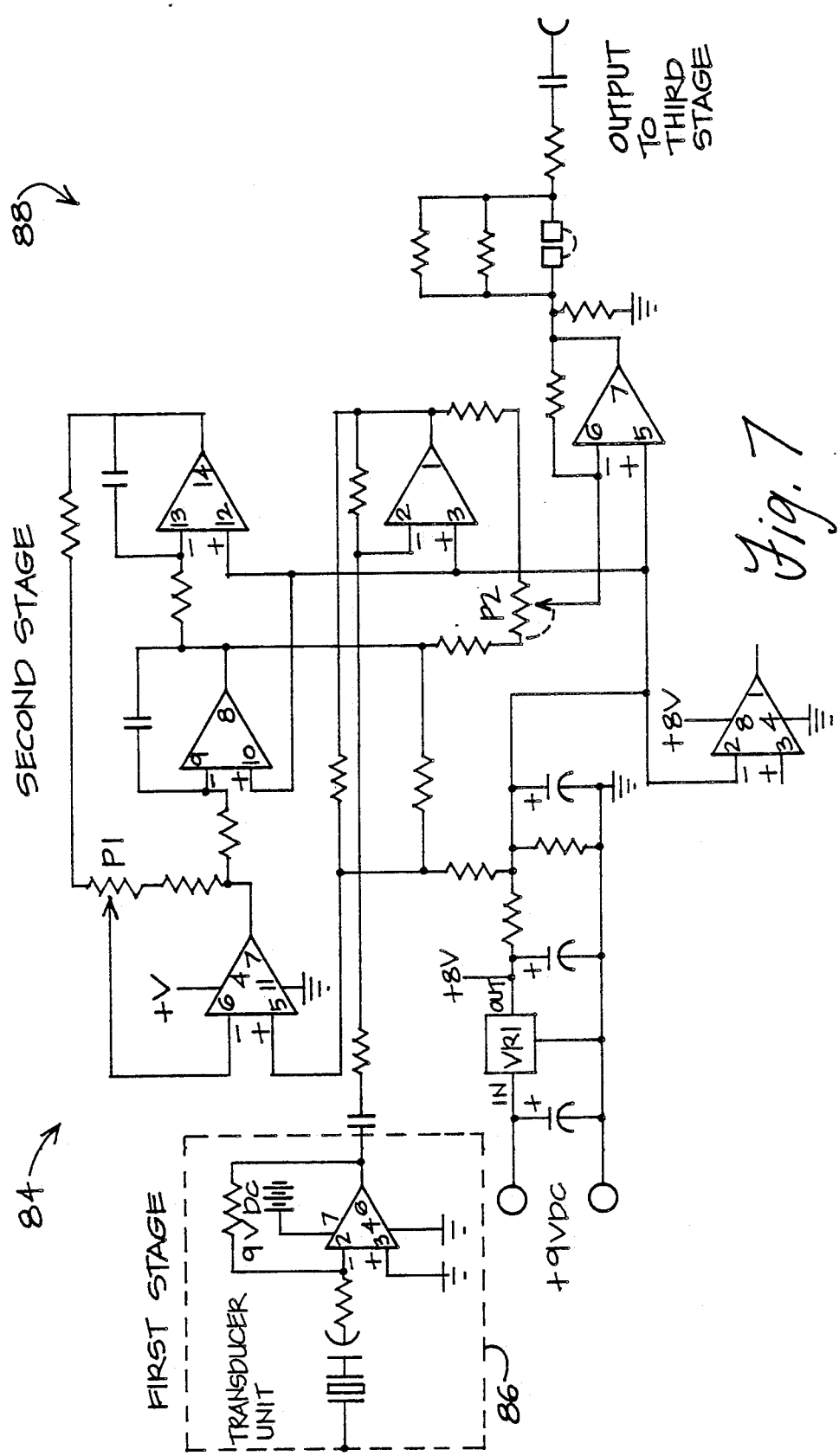
FIGS. 7 and 8 are schematic circuit diagrams of circuitry that may be employed in connection with the apparatus of the invention.
Figure 8:
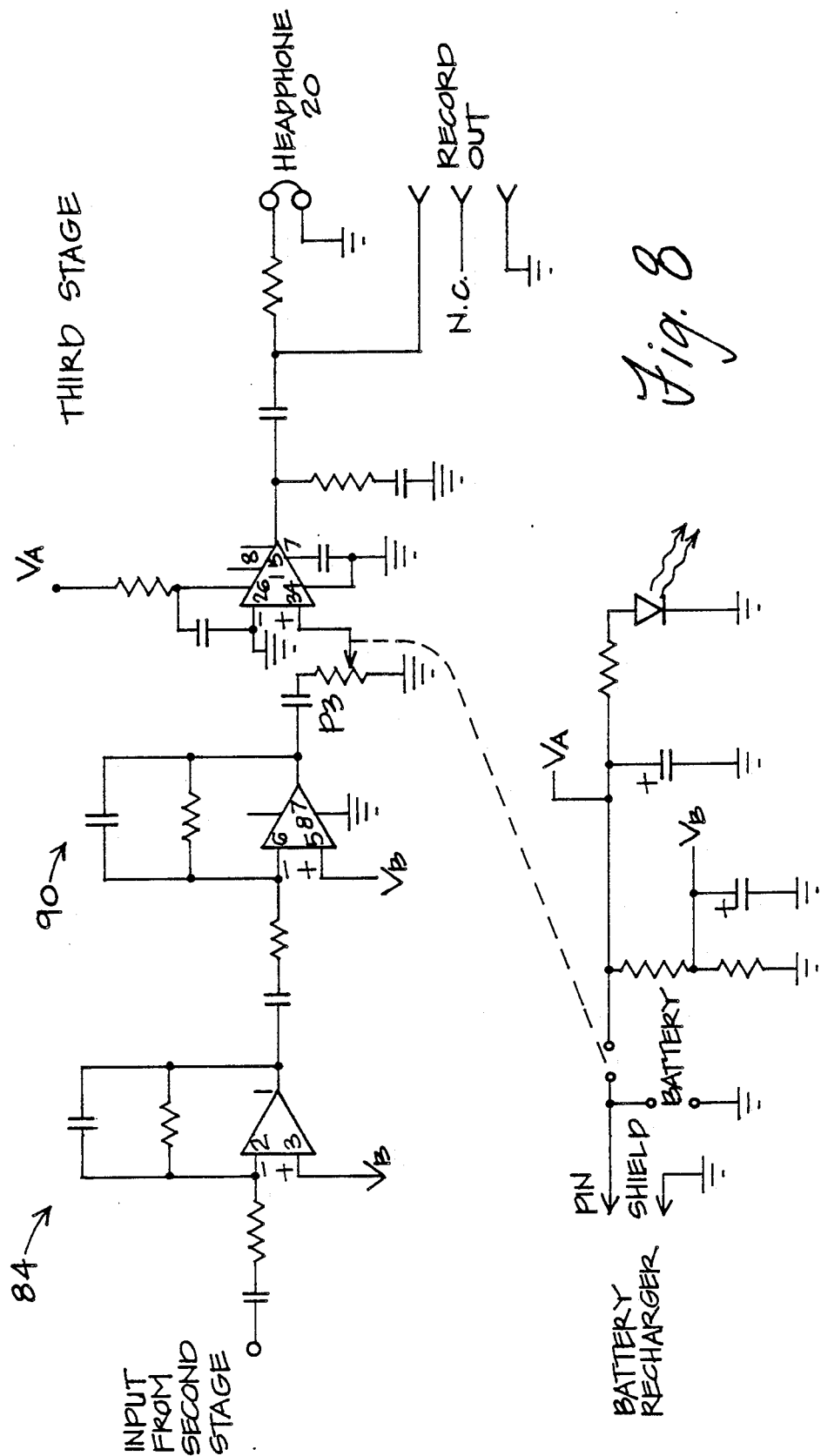

Circuits 44, 86, 88 and 90 may be energized by a 9 volt dry cell battery at each stage, connected with the positive input pins of the IC 1A amplifiers, and similar pins of the other amplifier components where indicated in FIGS. 7 and 8. Second stage 88 contains potentiometers P1 and P2, and third stage 90 has potentiometer P3. These potentiometers may be adjusted by using an oscilloscope, not shown, in a known manner. The desired audio signal output at the third stage 90 may be controlled by the settings of the potentiometers P1, P2 and P3, for example, if headset 20 is used. The headset 20 is preferably padded to eliminate extraneous sounds and to reduce feedback.

Each type of insect produces its own frequency rhythm when it feeds or moves within a certain particulate matter, such as a particular grain. This pattern can be heard through the headphones 20, or may be audio-recorded to be played back later and analyzed through a fast Fourier transform, spectrum analyzer, and oscilloscope and then processed through a computer or plotted on a graph.

With the printout of such graphs, it seems apparent that an operator can compare them with a known pattern, detect the difference between the patterns and identify a particular insect. In the absence of graphs, with a little practice an operator, by listening to magnetic tape records of known insects in a quantity of certain particulates, soon learns to distinguish between the vibrations produced in the particulate matter being monitored and with considerable accuracy is able to identify the type of insect.

OPERATION

In operation, referring to the embodiment seen in FIGS. 1 or 6, the user places the headset 20 over his ears and manually carries the transducer 14 using handle 18 and case 22. Circuit housing 12 may be clipped to the operator's person, or also held. The distal end 58 of probe 16 is then inserted using handle 18 into a quantity of particulate material, such as grain, that is contained by a bin, truck or other structure. In the embodiment illustrated in FIG. 5, a quantity of the particulate material is poured into bin 66, and the apparatus 10 is set alone to stabilize from the vibrations caused by the pouring actions.

Obviously, all extraneous or surrounding noises are, if possible, substantially eliminated prior to and during such tests. An advantage of the bin-type apparatus illustrated in FIG. 5 is that the sample may be physically transported to a quieter environment. When the probe-type apparatus, such as seen in FIG. 1 is employed, the quantity of grain must be tested at a number of different spots to be sure that insects are not missed.

It is apparent that the invention is susceptible to changes or alterations without defeating its practicability. Therefore, I do not wish to be confined to the preferred embodiment shown in the drawings and described herein.

I claim:

1. An apparatus for detecting the presence of insects in particulate matter comprising:
   (a) a vibration receiving structure;
   (b) a piezoelectric transducer means physically contacted by the vibration receiving structure at an off-center location on the transducer means for directly detecting the vibrations in the particulate matter via the vibration receiving structure and generating electrical signals in response to the detected vibrations;
   (c) means for selectively amplifying the portion of the electrical signals representative of the frequency range of vibrations generated by insects which may be present in the particulate matter; and
   (d) means for analyzing the electrical signals representative of the vibrations to identify the species within the particulate matter.

2. The apparatus of claim 1 where the vibration receiving structure is a long, solid probe for inserting into the particulate matter, where the length of the probe is many times that of its width.

3. The apparatus of claim 2 where the piezoelectric transducer is resiliently mounted.

4. An apparatus for detecting the presence of insects in particulate matter comprising:
   (a) a flat diaphragm forming at least one interior surface of a container for the particulate matter;
   (b) piezoelectric transducer means physically contacted by said diaphragm at an off-center location on the transducer means for directly detecting the vibrations in the particulate matter via the flat diaphragm and generating electrical signals in response to the detected vibrations;
   (c) means for selectively amplifying the portion of the electrical signals representative of the frequency range of vibrations generated by insects which may be present in the particulate matter; and
   (d) means for analyzing the electrical signals representative of the vibrations to identify the species within the particulate matter.

5. The apparatus of claim 4 where the piezoelectric transducer is resiliently mounted to the container.

6. An apparatus for detecting the presence of insects in particulate matter comprising:
   (a) a housing defining an exterior space from an interior space comprising:
      (1) a vibration receiving structure exposed to the exterior space;
      (2) a piezoelectric transducer means for
         (i) physically contacting the vibration receiving structure in an off-center location;
         (ii) directly detecting vibrations in the particulate matter via the vibration receiving structure; and
         (iii) generating electrical signals in response to the detected vibrations; and
      (3) mounting means for flexibly mounting the piezoelectric transducer means inside the housing;
   (b) means for selectively amplifying the portion of the electrical signals representative of the frequency range of vibrations generated by insects which may be present in the particulate matter; and
   (c) means for analyzing the electrical signals representative of the vibrations to identify the species within the particulate matter.

7. The apparatus of claim 6 where the vibration receiving structure is a solid, relatively long probe for inserting into the particulate matter, where the length of the probe is many times that of its width.

8. An apparatus for detecting the presence of insects in particulate matter comprising:
   (a) a housing defining an exterior space from an interior space comprising:
      (1) a flat diaphragm forming at least one interior surface of a container for the particulate matter exposed to the exterior space;
      (2) a piezoelectric transducer means for
         (i) physically contacting the vibration receiving structure in an off-center location;
         (ii) directly detecting vibrations in the particulate matter via the flat diaphragm; and
         (iii) generating electrical signals in response to the detected vibrations; and
      (3) mounting means for flexibly mounting the piezoelectric transducer means inside the housing;
   (b) means for selectively amplifying the portion of the electrical signals representative of the frequency range of vibrations generated by insects which may be present in the particulate matter; and (c) means for analyzing the electrical signals representative of the vibrations to identify the species within the particulate matter.

9. The apparatus of claim 8 wherein the flat diaphragm is made from hard flexible material responsive to vibrations typically associated with insects.

10. The apparatus of claim 8 where the piezoelectric transducer in physical contact with the flat diaphragm is positioned slightly out of the plane of the diaphragm thereby flexing the flat diaphragm.

11. The apparatus of claim 6 where the piezoelectric transducer means is substantially circular in design and is mounted at at least one mounting point such that the piezoelectric transducer means is unbalanced when pressure is applied at any point off center on any line segment defined by the center of the piezoelectric transducer means and the point or points of mounting between the piezoelectric transducer means and the mounting means.

12. The apparatus of claim 6 where:
(a) the piezoelectric transducer means is substantially square and is mounted at nonadjacent corners of the piezoelectric transducer means; and
(b) the point of contact between the piezoelectric transducer means and the vibration receiving structure is off the line between the nonadjacent corners of the square piezoelectric transducer means.

13. The apparatus of claim 6 where the mounting means comprises a resilient material.

14. The apparatus of claim 6 further comprising a pre-amplifier mounted close to the piezoelectric transducer means for minimizing 60 cycle hum induction.

15. The apparatus of claim 6, where the means for analyzing comprises means for comparing the vibrations with a known pattern of vibrations.

16. The apparatus of claim 6 where the means for analyzing comprise earphone means operatively connected to the amplifying means for listening to audible levels of the vibrations.

17. The apparatus of claim 6 where the means for selectively amplifying comprises filter means for filtering out noise and other signals except for signals representative of vibrations substantially between 350 and 3,500 Hertz.

18. A method for detecting the presence of insects in particulate matter comprising:
(a) directly sensing vibrations caused by insects in particulate matter by means of a vibration receiving structure in physical contact with the particulate matter;
(b) transducing the vibrations into electrical signals in response to the sensed vibrations by means of a piezolectric transducer means in off-center physical contact with the vibration receiving structure;
(c) selectively amplifying the portion of the electrical signals representative of the frequency range of vibrations generated by insects which may be present in the particulate matter; and
(d) analyzing the electrical signals representative of the vibrations to identify the species within the particulate matter.

19. The method of claim 18, where the step of analyzing comprises comparing vibration records generated by the apparatus with prerecorde records of known insect induced vibrations.

20. The method of claim 18 where the step of analyzing comprises listening to audible levels of the vibrations.

21. The method of claim 18 where the step of selectively amplifying comprises filtering out noise and other signals except for signals representative of vibrations substantially between 350 and 3,500 Hertz.

* * * * *